United States Patent [19]
Drocourt et al.

[11] Patent Number: 5,663,057
[45] Date of Patent: Sep. 2, 1997

[54] PROCESS FOR RAPID AND ULTRASENSITIVE DETECTION AND COUNTING OF MICROORGANISMS BY FLUORESCENCE

[75] Inventors: Jean-Louis Drocourt, Yerres; Patrick Desfetes, Saint Brice Sous Foret, both of France; Jaspal Sanghera, Foxton, United Kingdom

[73] Assignee: Chemunex, Maisons-Alfort, France

[21] Appl. No.: 493,130

[22] Filed: Jun. 21, 1995

[30] Foreign Application Priority Data

Nov. 17, 1994 [EP] European Pat. Off. ........... 94402610

[51] Int. Cl.$^6$ .......................... G01N 33/53; G01N 33/00; C12N 11/00; C12N 11/16
[52] U.S. Cl. .................... 435/40.5; 435/7.2; 435/7.32; 435/7.33; 435/7.34; 435/7.35; 435/174; 435/176; 435/287.1; 435/968; 436/518; 436/10; 436/800
[58] Field of Search .................... 435/7.2, 7.32, 435/7.33, 7.34, 7.35, 174, 176, 240.2, 240.23, 240.241, 240.25, 288.1, 288.3, 287.1; 436/518, 524, 100, 800

[56] References Cited

U.S. PATENT DOCUMENTS

| | | | |
|---|---|---|---|
| 4,180,831 | 12/1979 | Morton et al. | 358/160 |
| 4,647,531 | 3/1987 | Kamentsky . | |
| 4,745,285 | 5/1988 | Recktenwald et al. | 250/458.1 |
| 4,845,552 | 7/1989 | Jaggi et al. | 358/93 |
| 4,845,653 | 7/1989 | Conrad et al. | 364/521 |
| 5,093,866 | 3/1992 | Douglas-Hamilton et al. . | |
| 5,103,101 | 4/1992 | Berglund et al. . | |
| 5,246,829 | 9/1993 | Delaage et al. | 435/2 |
| 5,428,441 | 6/1995 | Ogino et al. | 356/73 |

OTHER PUBLICATIONS

Breeuwer et al., Energy-Dependent, Carrier-Mediated Extrusion of Carboxyfluorescein from *Saccharomyces cerevisiae* Allows Rapid Assessment of Cell Viability by Flow Cytometry, Applied and Environmental Microbiology, 60(5), 1467–1472. 1994.

Breeuwer et al., Characterization of Uptake and Hydrolysis of Fluorescein Diacetate and Carboxyfluorescein Diacetate by Intracellular Estrases in *Saccharomyces cerevisiae*, Which Result in Accumulation of Fluorescent Product, Applied and Environmental Mic 1995.

Diaper et al., Rapid Assessment of Bacterial Viability by Flow Cytometry, Applied Microbiology Biotechnology, 38, 268–272 1992.

(List continued on next page.)

*Primary Examiner*—Christopher L. Chin
*Assistant Examiner*—Bao-Thuy L. Nguyen
*Attorney, Agent, or Firm*—Oblon, Spivak, McClelland, Maier & Neustadt, P.C.

[57] ABSTRACT

Process for rapid, ultrasensitive and automatic counting of fluorescent biological cells such as microorganims, carried by a solid support such as a filter.

The process includes: scanning a solid support on which a specimen potentially containing microorganisms has been deposited, with an incident beam from a laser, forming a laser spot on the solid support, the laser spot being substantially greater than the microorganisms to be detected, the laser spot size being between 4 and 14 μm and simultaneously: detecting the resultant fluorescent light at least at one wavelength; establishing a set of correlated-features by a line-to-line correlation of individual features; comparing said correlated-features on each pair of adjacent lines in time synchrony, at least at two different wavelengths $\lambda_1$ and $\lambda_2$; making a size discrimination of retained events and selecting those having a size corresponding to a microorganism; determining if for retained events after size discrimination, the events energy profile in three dimensions is within predetermined Gaussian shape criteria; and counting said remaining events to determine and to count exclusively the microorganisms present on said solid support.

4 Claims, 11 Drawing Sheets

OTHER PUBLICATIONS

Jaggi et al., The Design and Development of an Optical Scanner for Cell Biology, Proceedings of the Seventh Annual Conference of the IEEE/Engineering in Medicine and Biology Society, 2, 980–985. 1985.

Jaggi et al., Implementation and Evaluation of the DMIPS Cell Analyser, 2, 906–911. 1986.

Kaplow, L., Assessment of Leukocyte Alkaline Phosphatase by Image Analysis, Clinical Cytometry, 468, 85–92. 1986.

Kaprelyants et al., Rapid Assessment of Bacterial Viability and Vitality by Rhodamine 123 and Flow Cytometry, Journal of Applied Bacteriology, 72, 410–422. 1992.

Mayall, B., Cytometry in the Clinical Laboratory: Quo Vadis?, Clinical Cytometry, 468, 1–17. 1986.

Palcic et al., The Use of Solid–State Image Sensor Technology to Detect and Characterize Live Mammalian Cells Growing in Tissue Culture, 50(2), 345–352. 1986.

Spadinger et al., Automated Detection and Recognition of Live Cells in Tissue Culture Using Image Cytometry, Cytometry, 10, 375–381. 1989.

Optical Engineering, vol. 32, No.2, Feb. 1993 Bellingham US, pp. 306–313, K.P. Roos et al "High–speed video imaging and digital analysis of microscopic features in contracting striated muscle cells".

| File Name: | bnhs_11.002 | | Time: | Wed Jul 13 07:36:52 1994 |
|---|---|---|---|---|

| Laser: | 50mW | | PMT1: 750V | PMT2: 930V |
|---|---|---|---|---|

| | Width (lines) | Length (samples) | Peak Intensity (ADC counts) | Mean Intensity (ADC counts) |
|---|---|---|---|---|
| | 3 | 16 | 68 | 39.8 |
| Mean: | 0.9428 | 2.285 | 20.37 | 3.51 |
| Std dev. | | | | |

| Green: | Events and single features | 55 | Spots rejected because of: | |
|---|---|---|---|---|
| Red: | Events and single features | 30 | Single features: | 18 |
| Result: | EVENTS | 19 | Red/Green Ratio: | 17 |
| | | | Size: | 1 |
| | | | Gaussian: | 0 |

*FIG. 11*

PROCESS FOR RAPID AND ULTRASENSITIVE DETECTION AND COUNTING OF MICROORGANISMS BY FLUORESCENCE

FIELD OF THE INVENTION

The present invention relates to an apparatus for rapid, ultrasensitive and automatic counting of fluorescent biological cells such as microorganims, carried by a solid support such as a filter and to a process for said rapid count of said microorganisms by said apparatus.

BACKGROUND OF THE INVENTION

The analysis of biological samples, food samples, potable water samples and pharmaceutical products for the presence of microorganisms is important and has important ramifications for safety, quality regulations and public health. For instance, recent oubtbreaks of food borne illness, implicating cheese and other dairy products contaminated with pathogenic bacteria, underscore the need for rapid methods for microbiological analysis.

In the traditionnal plate technique, a sample to be analyzed is cultured and the resulting colonies counted. The results of the test are obtained after a growth period ranging from a minimum of 1 day to as much as 7 to 8 days. In this technique, the growth period provides at one time, the distinction between viable and non-viable organisms, as well as the magnification of the signals from the viable organisms, to facilitate their detection at low concentration.

There is a crucial need for more rapid, more sensitive and more automated methods, for industrial as well as medical applications.

Rapid methods have been developed which are based on measuring the consequence of the metabolic activity of the microorganisms on a bulk property of the sample, such as impedance. All of these methods, called indirect methods, suffer from reduced sensitivity and still require culturing when the detection of low levels of contamination is required.

Other methods based on the direct counting of microorganisms have been developed recently. Among these, the direct epifluorescent filter techniques (DEFT) may be cited. In this technique the specimen to be analyzed is caused to pass through a filter which retains the microorganisms. The microorganisms are then made fluorescent and counted by visually analyzing the filter surface with an epifluorescence microscope. In this method, particles of interest are generally labelled with a fluorescent dye, such as acridine orange or other more specific dyes.

The visual analysis is tedious and complicated: first, because in the absence of a growth phase the organisms are quite small (requiring high power magnification for their detection), and second because the total area of the filter is so large that an impractical number of high power fields are required to cover the whole filter. Thus, typically only a small part of the filter is visually examined (less than 10%). This makes the technique inappropriate for sterility testing, where one single microorganism on the total filter has to be detected.

An additional problem with the DEFT technique is discrimination between the searched microorganisms and other particles, which are naturally fluorescent, that may have also been concentrated on the filter.

As a result of these problems, the repeatability and accuracy of the DEFT method are generally lower than that of the plate count methods. Other limitations of the DEFT include, low sensitivity, fading of intensity and operator fatigue, from prolonged use of the microscope.

The use of the epifluorescent microscope fitted with an image analyzer, in view to improve the DEFT technique has also been reported. However, although this is effective in eliminating subjectivity and operator fatigue, it is still limited by the fundamental problem that the organisms are small and the area to be covered is large.

In order to better understand this problem, it is useful to note that in electronic imaging systems the resultant image is made up of individual picture elements (pixels). In the current state of the art of electronic imaging, even the best video cameras can only form images of as many as 100,000 or 1 million pixels. However, the diameter of a single microorganism is typically around 1 µm while the diameter of the filter is 25,000 µm. Thus, if we consider one pixel to be the size of a microorganism, it would take 625 million pixels to cover the entire filter.

As a result either a single picture element (pixel) must be made much larger than the dimensions of a single microorganism or the analysis must include many sequential images. However, neither of these approaches is satisfactory. In the first case, the sensitivity of detection is lowered while, in the second case the time and complexity of analysis are limiting factors.

Another known means to improve the DEFT technique which may be considered is the use of a scanning confocal epifluorescence microscope. In this apparatus, a small laser spot is used to sequentially illuminate each element of the image field, while a detector positioned behind a small pinhole is also focused on the same element. The image is then formed from the detector signals in a manner similar to that described above for an electronic imaging system. In the optimum design of such an apparatus the dimensions of the illuminating spot is less than or equal to the dimensions of the smallest particle to be detected, and the dimensions of the pinhole is equal to or smaller than the dimensions of the illuminating spot.

The use of this known technology of scanning confocal microscopy is also not appropriate for this application, for at least the following reasons:

1) As stated above the ratio of the size of the filter to the area of the microorganism is greater than 100 million. Thus either a spot much larger than the organism must be used (with attending loss of sensitivity) or the scan time must be impractically long.

2) In practical industrial samples, the membranes are both thick and not flat. Thus the microorganisms may be trapped at different levels in the pores of the filter membrane. As a result the region of the filter wherein the microorganisms of interest are trapped is not sufficiently well defined along the optical axis to permit the focusing optics to limit the depth of field which is a result of the insertion of a pinhole in front of the detector.

3) An apparatus based on the above technology, performing high resolution scan of the entire filter would be very complex and expensive, and hence not practical for routine use.

Thus, in summary the known means of electronic image analysis either through the use of a video camera, a scanning apparatus, or combinations of these techniques are not suitable to the automation of the DEFT technique principally because of the large ratio between the size of the filter and the size of a single microorganism.

SUMMARY OF THE INVENTION

The present invention relates to an apparatus and a process capable of rapid and complete counts of fluorescent microorganisms such as those that might be trapped on the filter in the DEFT technique. The entire surface of the solid support such as a filter membrane is scanned with a laser beam and the fluorescence emitted measured at one or more wavelengths. In the invention, the drawbacks described above are overcome through the use of a different and unique scanning pattern in combination with a unique means of processing the extensive detector signal data obtained in scanning the entire filter. In the invention a larger scanning spot is used together with an overlapping scan pattern which act together to maintain the sensitivity typically associated with a smaller spot while permitting a rapid scan.

Furthermore, the present invention avoids both false negative and false positive results. It provides a process to fully discriminate wanted from unwanted signals, resulting in an accurate and fast counting of microorganisms present on a solid support of large dimension (typically 25 mm diameter), even at very low numbers. The invention has the potential to unequivocally detect down to one microorganism on the filter.

In order to understand the invention, it is instructive to note that the probability of detection for N independent scan passes over a target is proportional to the square root of N times the probability of detection for a single pass. The probability of detection for a single pass is in turn inversely proportional to the speed at which the pass is made. Thus, in general, scanning the field twice, at twice the speed, is equivalent in probability of detection to scanning once and no net gain in scan time is realized. However, if the two passes are added in time synchrony, they are no longer independent trials, and a signal event, (which will be correlated between the two passes), will be favored over a noise event, (which will be uncorrelated). Thus, increasing the probability of detection and permitting a decrease in the scan time.

In the invention, an increased scanning rate is accomplished, for instance, by scanning with a large laser spot (see FIG. 1), and overlapping the scan, such that each element in the field is scanned at least twice. The results of each adjacent pair of scans in the X direction are then compared in time synchrony for the purpose of maintaining the probability of detection by eliminating uncorrelated signals. Thus, each positive event is correlated between two or more scan lines, (depending on the size of the fluorescent object).

Definitions

As the laser spot moves along scan lines on the solid support (such as a filter membrane) the fluorescence light emitted (if any) is measured continously by one or more detectors (at various wavelengths). The analog signal coming out of the detectors is digitalized by taking its value at constant frequency intervals.

Reading: a reading is the value of the signal at the time of measurement.

Sample: a sample is defined as a reading of the signal from the detector which exceeds a given dynamic threshold.

Feature: a set of adjacent samples on one scan line is called a feature.

Line to line correlation: 2 samples are said to be correlated when they appear in time synchrony on two adjacent scan lines.

Single feature: a feature which appears on only one scan line, ie which is not correlated, is called a single feature.

Fluorescent spot: fluorescence emitted by any fluorescent particle when excited by a laser beam. These particles can be microorganisms or other elements such as dust.

The particles can be autofluorescent or have been made fluorescent for the detection (for example, microorganisms).

Event: an event is a set of at least two features which are correlated in time synchrony on adjacent scan lines.

An event is the translation of a fluorescent spot in the measurement process.

An event may subsequently be classified by the discriminator as either a positive event (ie an event being searched, such as a microorganism) or as a noise event (ie an event to be rejected as due to fluorescence generated for example by autofluorescent particles). A noise event, if included in the final count, would give false positives.

Laser spot: light spot formed by a laser beam on a solid support.

Interline or line spacing Y: distance between two scanning lines.

Some of said definitions are illustrated in FIG. 2, in which samples are represented by ○ and in which the length of an event (set of correlated-features) corresponds to the number of accumulated count of samples from the start of the feature occuring the earliest in a scan-line in the scan direction, and the end of the feature which terminates the latest in a scan line, said counting taking as one sample all the correlated samples on different scan lines, and the width of an event is defined by the number of adjacent lines on which the same event appears.

In one aspect of the present invention, a method for counting fluorescent microorganisms on a solid support (or specimen support) such as a filter membrane, is provided. Said method is characterized in that it comprises:

scanning a solid support on which a specimen potentially containing microorganisms has been deposited, the said specimen having been subject to fluorescent staining, with an incident beam from a laser, forming a laser spot on the solid support, said laser spot being substantially greater than the microorganisms to be detected, said laser spot size being comprised between 4 and 14 μm, wherein the distance between two scanning lines is such that each element of the support is scanned at least twice, by partial overlapping of adjacent scanning paths and is preferably less than half the dimension of said laser spot size; and simultaneously:

detecting the resultant fluorescent light at least at one wavelength, by selecting only detected signals exceeding a given threshold (=samples), for instance a dynamic threshold, wherein a set of adjacent samples on a scan-line represents a feature;

establishing a set of correlated-features by a line-to-line correlation of individual features, by comparing features on each pair of adjacent lines in time-synchrony, counting the number of lines over which said set of correlated-features occur, each set of correlated-features forming an event, and eliminating any single uncorrelated-features;

correlation is considered as existing when one or more samples within the two features under comparison are detected in the same position on said pair of lines. The number of lines over which said set of correlated-features occur is counted, and thereafter used in size discrimination;

comparing said correlated-features on each pair of adjacent lines in time synchrony, at least at two different wavelengths $\lambda_1$ and $\lambda_2$, for selecting the correlated-features having an emission intensity ratio at said two wavelengths lower than a predetermined number, being specified that if the emission ratio at said wavelengths generated by any correlated-samples is greater than a predefined value, the complete event is eliminated;

making a size discrimination of retained events and selecting those having a size corresponding to a microorganism;

determining if for retained events after size discrimination, the events energy profile in three dimensions is within predetermined Gaussian shape criteria and rejecting events not within said predetermined Gaussian shape criteria. Such analysis is for instance performed by a software curve-fitting algorithm. All events within the criteria are accepted as microorganism for the final count; those outside the criteria are classified as noise (dust or other contaminants on said solid support);

counting said remaining events to determine and to count exclusively the microorganisms present on said solid support.

The expression "size-discrimination" means that only events having a given number of correlated-features and a given number of samples are retained towards the final counts. In such case, the instant process comprises evaluating the number of scan lines covered by one event (width) and the number of samples forming the length of the event; this latter number deriving from accumulated count of samples from the start of the feature occuring the earliest in a scan-line in the scan direction, and the end of the feature which terminates the latest in a scan line, counting as one any sample appearing at the same location on 2 or more adjacent lines. Events are eliminated if comprising such overall sample count length greater than a predetermined number A, and a number of scan-lines greater than a predetermined number B (refer to FIG. 2).

More precisely, according to a preferred embodiment of said aspect of the invention, said size discrimination is carried out by:

determining the length of each event by counting the number of samples, by starting with the sample appearing first on the scanning direction on whatever feature of said event occuring the earliest, continue to include the sample appearing last in the scan direction on whatever feature ends last, said counting taking as one sample all the correlated samples on different scan lines, determining the width of said event by counting the number of adjacent lines covered by the same event and eliminating events for which the number of said counted samples is greater than a predetermined number A, and/or the number of said adjacent scan-lines is greater than a predetermined number B.

In another aspect of the present invention, the instant process is characterized in that it comprises:

collecting microorganisms from a specimen on a solid support, such as a filter membrane;

labelling said microorganisms with a dye selected from the group constituted by vital dyes, viability markers, fluorescence substances carried by antibodies or nucleic probes, or generated by an enzyme linked probe system, capable, when excited, to produce an emission fluorescent at a wavelength $\lambda_1$;

scanning said solid support with an incident beam from a laser, forming a laser spot on said solid support, said laser spot being substantially greater than the microorganisms to be detected, said laser spot size being comprised between 4 and 14 µm, wherein the distance between two scanning lines is such that each element of the support is scanned at least twice by partial overlapping of adjacent scanning paths and is preferably less than half the dimension of said laser spot size, and simultaneously:

detecting the resultant fluorescent light at least at one wavelength, by selecting only detected signals exceeding a given threshold (=samples), wherein a set of adjacent samples on a scan-line represents a feature;

establishing a set of correlated-features by a line-to-line correlation of individual features, by comparing features on each pair of adjacent lines in time synchrony, counting the number of lines over which said set of correlated-features occur, each set of correlated-features forming an event, and eliminating any single uncorrelated-features;

correlation is considered as existing when one or more samples within the two features under comparison are detected in the same position on said pair of lines. The number of lines over which said set of correlating-features occur is counted, and thereafter used in size discrimination;

comparing said correlated-features on each pair of adjacent lines in time synchrony, at least at two different wavelengths $\lambda_1$ and $\lambda_2$ for selecting the correlated-features having an emission intensity ratio at said two wavelengths lower than a predetermined number, being specified that if the emission ratio at said wavelengths generated by any correlated samples is greater than a predefined value, the complete event is eliminated;

making a size discrimination of retained events and selecting those having a size corresponding to a microorganism;

determining if for retained events after size discrimination, the events energy profile in three dimensions is within predetermined Gaussian shape criteria and rejecting events not within said predetermined Gaussian shape criteria. Such analysis is for instance performed by a software curve-fitting algorithm. All events within the criteria are accepted as microorganism for the final count; those outside the criteria are classified as noise (dust or other contaminants on said solid support);

counting said remaining events to determine and to count exclusively the microorganisms present on said solid support.

The expression "size-discrimination" has the same meaning as above.

More precisely, according to a preferred embodiment of said aspect of the invention, said size discrimination is carried out by:

determining the length of each event by counting the number of samples, by starting with the sample appearing first on the scanning direction on whatever feature of said event occuring the earliest, continue to include the sample appearing last in the scan direction on whatever feature ends last, said counting taking as one sample all the correlated samples on different scan lines, determining the width of said event by counting the number of adjacent lines covered by the same event and eliminating events for which the number of said counted samples is greater than a predetermined number A, and/or the number of said adjacent scan-lines is greater than a predetermined number B.

As stated hereabove, the distance between two scanning lines (interline or line spacing y) is less than half the dimension of said laser spot size, leading to an overlap of the scanned surface.

Preferably, the step of detecting the resulting fluorescent light is performed by measuring signals exceeding a dynamic threshold, by means of a digital signal processor (DSP).

Said DSP allows to differentiate between wanted signals (corresponding to microorganisms) and some unwanted signals (electronic noise for instance).

Such a process avoids, unexpectedly, both false negative and false positive results.

The following Table I summarizes the potential causes for false negative or false positive results and the relevant steps of the instant process to eliminate the errors.

TABLE I

|  | Possible causes | Relevant steps for correction |
| --- | --- | --- |
| False positive | PMT noise<br>Background fluo-<br>rescence of<br>filter<br>Autofluorescent<br>dirt or particle<br>having absorbed<br>the dye | Line to line<br>correlation<br>Gaussian curve<br>Dynamic thresholding<br>Colour<br>discrimination<br>Size discrimination |
| False negative | Area not covered<br>Bacteria signal<br>not discriminated<br>above background<br>Bacteria assigned<br>as PMT noise or<br>dirt | Overlapping and full<br>filter scanning<br>Background level<br>thresholding<br>Colour discrimination<br>Line to line<br>correlation<br>Size discrimination |

It must be highlighted that the present process handles only with fluorescent spots and identifies fluorescently-labelled bacteria by analysis of the label's fluorescent response to a scanning laser. The analysis technique makes use of fluorescence discrimination comprising:

evaluation of the number of adjacent samples on a scan line (=feature), line to line correlation and number of correlated features in view to make a "size discrimination" as defined hereabove and to provide an accurate detection of microorganisms.

Therefore, the instant analysis technique makes use of the size of the object to detect only in the following two ways:

the fluorescent response on any single scan line must be large enough to exceed a predetermined noise threshold;

a feature must be detected with a predetermined degree of overlap on at least two consecutives line scans.

These requirements mean that the instant process differs markedly from imaging systems, which require significantly more information on the shape and size of a feature.

These requirements drive the design of an imaging system towards small laser spot size, in order that the spot is smaller than the object being detected. The instant spot size can be large relative to the feature, and is currently of the order of 10 times the feature size. This gives major benefits in sampling speed, optical accuracy requirements, and processing power (data handling rate and memory requirements).

Unexpectedly, the instant process provides:

dynamic thresholding of signal level: the data processing system continuously monitors background noise level, and adjusts the threshold level which features must exceed to be regarded as significant. This allows the system to tolerate variation in the behaviour of the membrane (solid support), both from membrane to membrane, and over the area of a single membrane;

line-to-line correlation of signals: in order to be assigned as microorganism, features must be present on at least two scan lines;

use of a green fluorescence spectrum shape for feature discrimination (red/green signal level). A feature detected in the green channel must have a corresponding red channel signal small or nil, as predicted from the shape of the green fluorescent marker emission spectrum. A higher level of red channel response will cause the feature to be rejected;

signal discrimination: signals must be present for a predetermined number of scan points in order to be acceptable. Short signals are rejected as noise;

correlated features comprising above a predetermined number of samples or above a predetermined number of lines (i.e., either along a given scan line, or across several line scans) are rejected.

In another aspect of the present invention, an apparatus for detection and counting of microorganisms by fluorescence on a solid support is provided.

Said apparatus is characterized in that it comprises:

a laser light source for emitting an incident light beam, cooperating with means for focusing said laser beam into a laser spot, the dimension of which on a solid support is substantially greater than the microorganisms to be detected and counted, said laser spot size being comprised between 4 and 14 µm;

scanning means for directing the light from said light source onto said solid support to spotwise irradiate the microorganisms to produce fluorescence spots, wherein the distance between two scanning lines is such that each element of the support is scanned at least twice, by partial overlapping of adjacent scanning paths and is preferably less than the dimension of said laser spot size;

means for detecting and photoelectrically converting said emitted fluorescence at least at two different wavelengths $\lambda_1$ and $\lambda_2$;

means for discriminating and eliminating non-bacterial fluorescence including a digital signal processor and a plurality of optic paths for selecting at least two emission fluorescence wavelengths;

signal processing means for establishing sets of correlated-features by a line-to-line correlation of individual features, by comparing features on each pair of adjacent lines in time synchrony, counting the number of lines over which said set of correlated-features occur, each set of correlated-features forming an event, and eliminating any single uncorrelated features, occuring only on one line; comparing said correlated-features on each pair of adjacent lines in time synchrony, at least at two different wavelengths $\lambda_1$ and $\lambda_2$, for selecting the correlated-features having an emission intensity ratio at said two wavelengths lower than a predetermined number, being specified that if the emission ratio at said wavelengths generated by any correlated features is greater than a predefined value, the complete event is eliminated; making a size discrimination of retained events and selecting the events having a size corresponding to a microorganism; determining if for retained events after size discrimination, the events energy profile in three dimensions is within predetermined Gaussian shape criteria and rejecting events not within said predetermined Gaussian shape criteria, and counting said remaining events to determine and to count exclusively the microorganisms present on said solid support.

Said apparatus allows that the entire surface of the solid support is scanned.

According to one aspect of said apparatus, said scanning means comprises a first oscillating mirror, the axis of oscillation of which is perpendicular to the axis of the light beam for scanning a line by the beam; and a second mirror, the axis of which is perpendicular to the axis of oscillation of the first mirror, said second mirror executing a scanning movement synchronized with the scanning movement of said first mirror.

According to another aspect of the apparatus, said detecting means includes at least two photo-multipliers as a means for the photoelectric conversion.

According to another aspect of the apparatus, said laser spot has an elongated shape.

According to another aspect of the apparatus, said solid support is a filter membrane.

According to another aspect of the apparatus, said sample holder cooperates with cooling means, such as ones leading to Peltier effect.

In addition, a thin layer of a material such as silicon may be sandwiched between said sample holder and said filter membrane.

Said thin layer has, for instance, the following advantages: no autofluorescence, low light reflexion at the excitation wavelength and easy to clean.

The following figures can be used to describe the means by which the invention was reduced to practice.

BRIEF DESCRIPTION OF THE DRAWINGS

FIGS. 11 and 12: illustrate results obtained with the instant process in the detection of bacteria in water with a viability marker in one experiment.

FIG. 11 provides the setting of the instrument and the number of events detected and reported (19 in this experiment).

FIG. 12 shows the localisation of the microorganisms.

DESCRIPTION OF PREFERRED EMBODIMENTS

Figure 3:
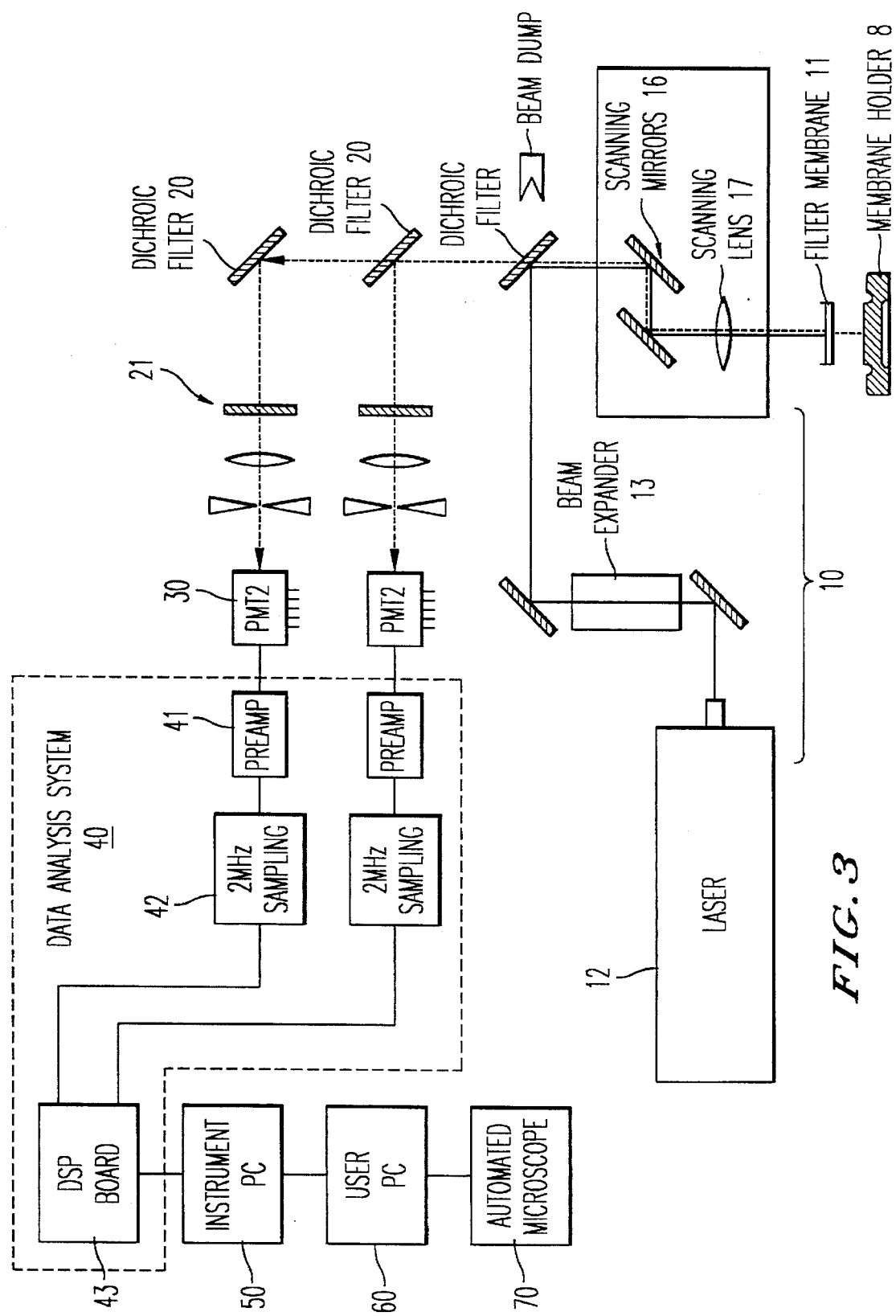
FIG. 3: sketch of the apparatus showing the laser, optics, scanning mirrors, specimen support, specimen support holder, detectors, and a black box for post detection electronics.
Figure 4:
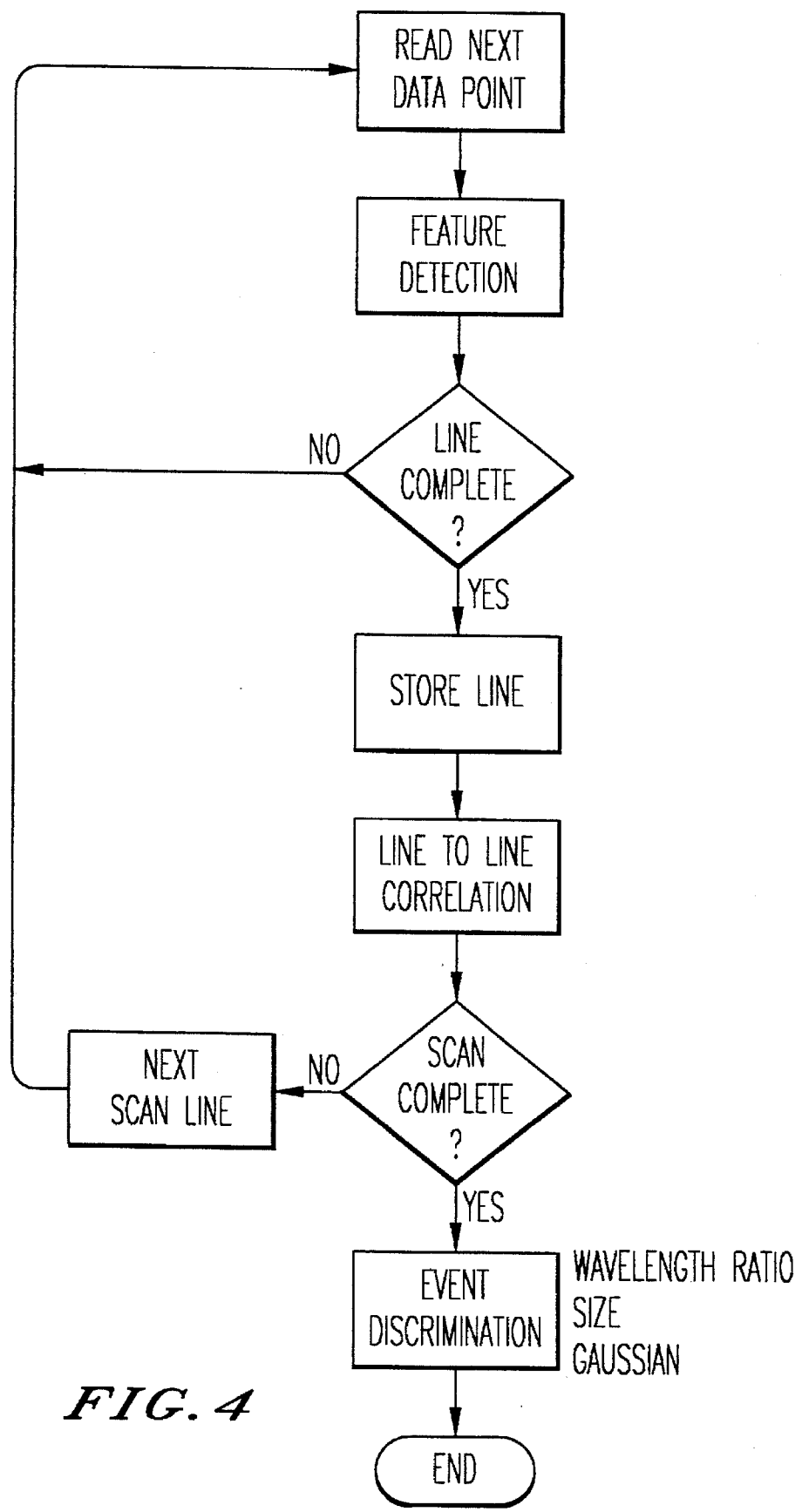
FIG. 4: flow chart showing top level control algorithm.
Figure 5:
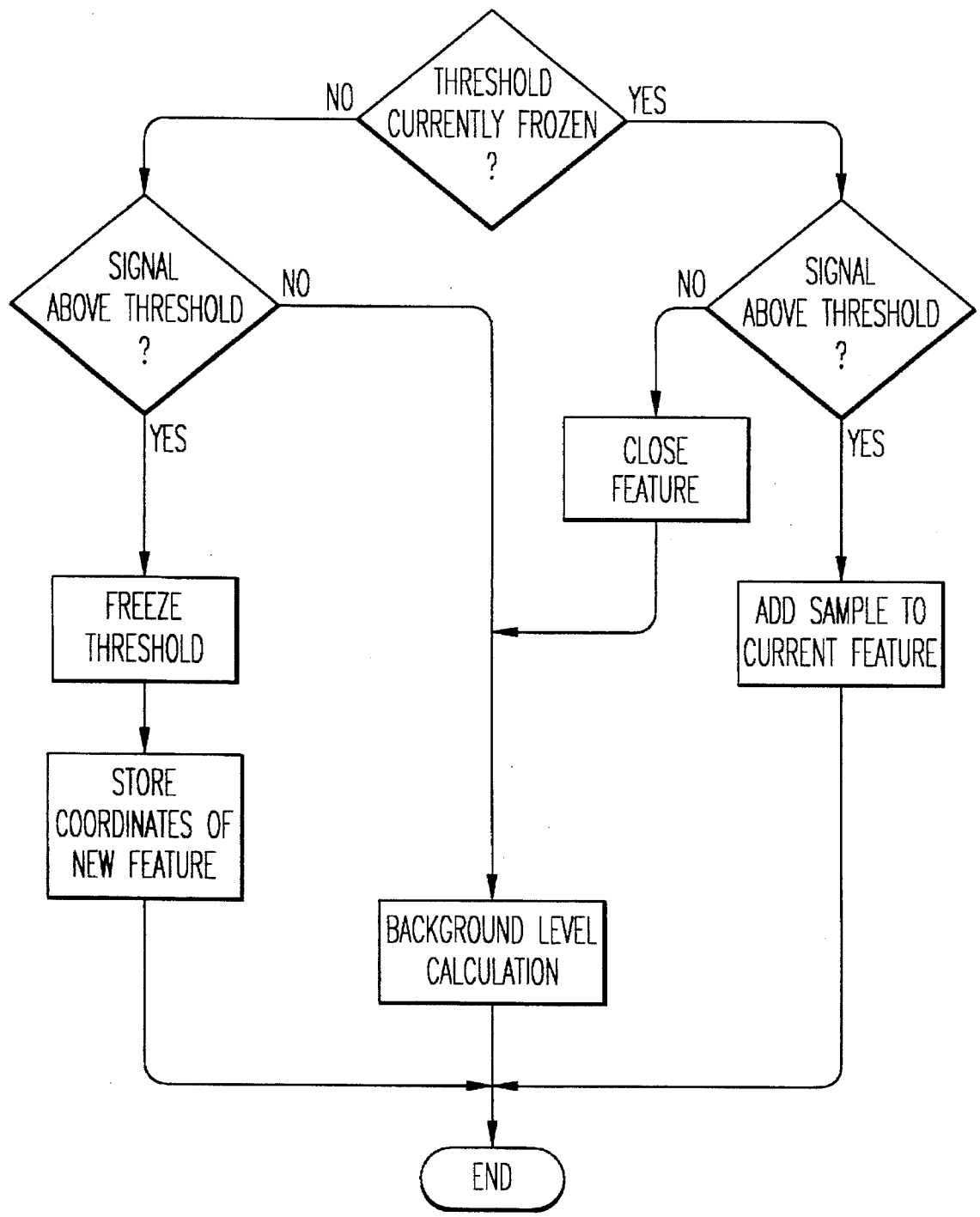
FIG. 5: flow chart showing feature detection.
Figure 6:
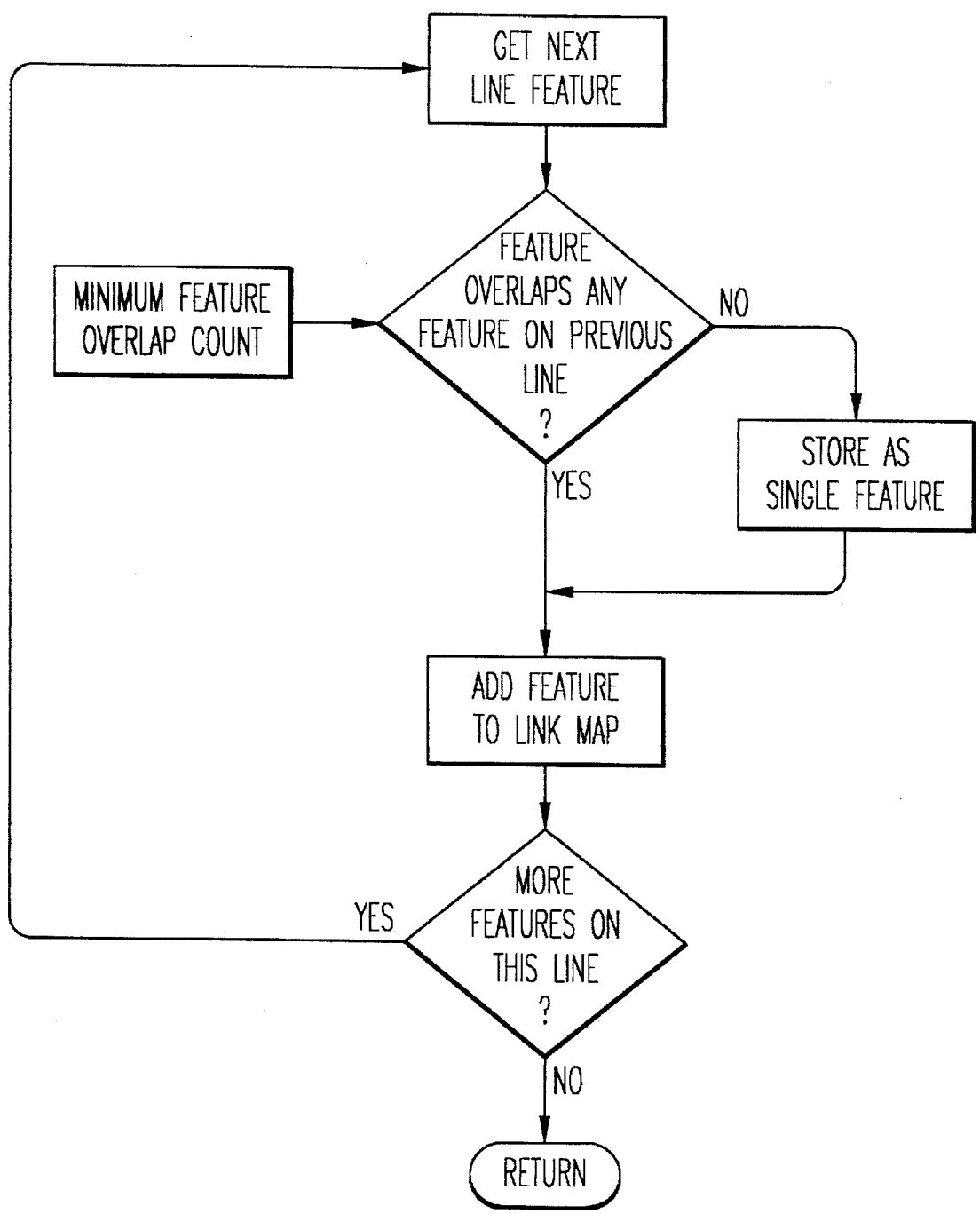
FIG. 6: flow chart showing line correlation.
Figure 7:
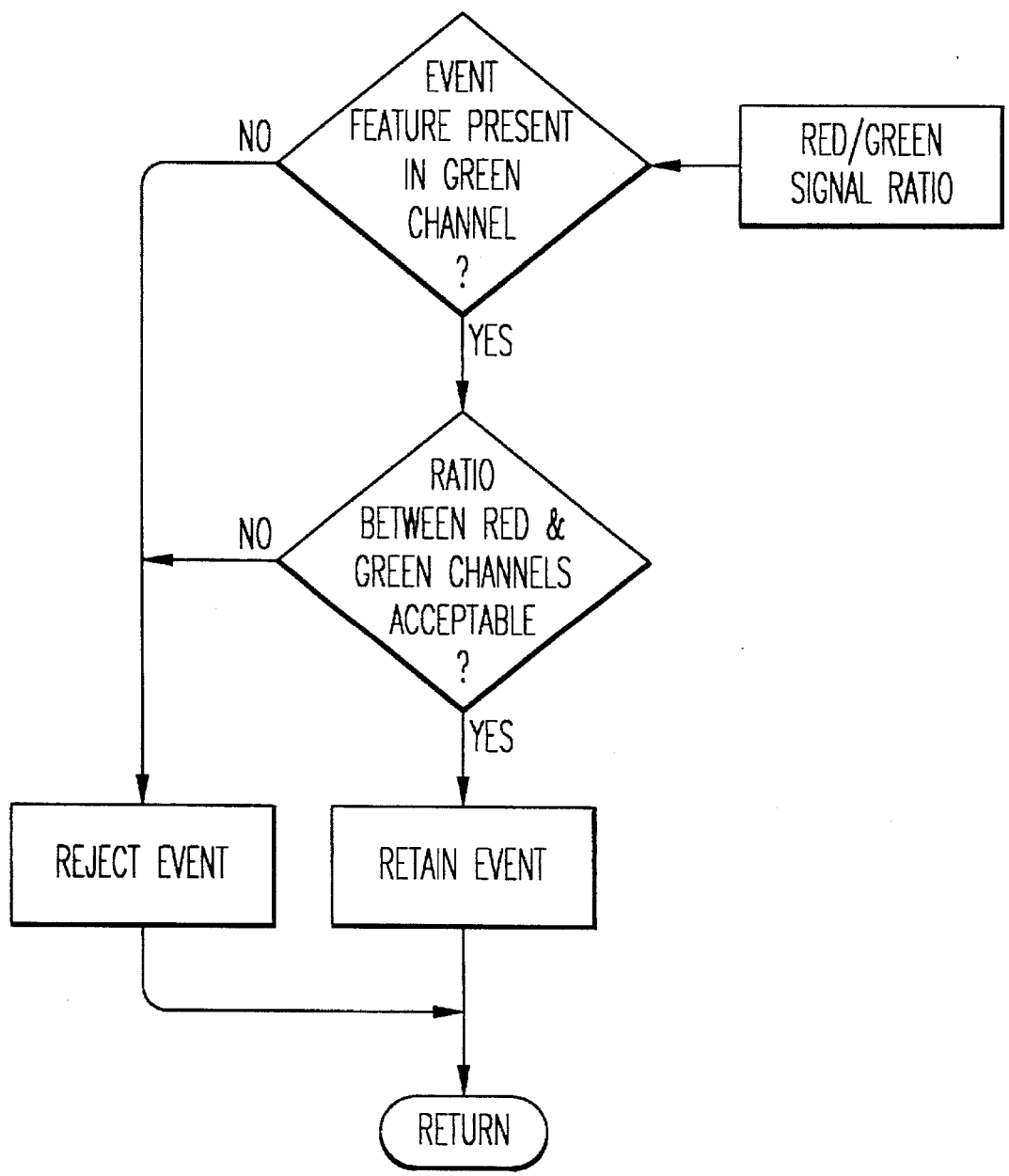
FIG. 7: flow chart showing color ratio discrimination.

Referring to FIG. 3, there is shown an apparatus according to the invention comprising scanning means 10, means for detecting the emitted fluorescence, including dichroic filters 20, optical filters 21, photo-multipliers (PMT) 30, a signal processing system 40–42, a digital signal processor 43, an instrument PC 50, a user PC 60 and an automated microscope 70.

The scanning device 10 uses coherent light to scan a solid support 11, represented by a filter membrane, carried on a membrane holder 8.

In the preferred embodiment, the components of the scanning device 10 include a 488 nm argon-ion water cooled laser 12, scan mirrors 16, scanning lens 17 and a beam dump 18 which is a safety feature; said scanning means cooperates with means for focusing said laser beam into a laser spot comprising a beam expander 13 which controls the illuminating spot size to 4–14 µm, preferably 7 µm, and directs the illuminating spot onto said scan mirrors 16.

Said beam expander 13 comprises two lenses, adapted (focal distance and distance between said two lenses), such as providing a laser spot on said solid support from 4 to 14 µm; for instance, to obtain a laser spot of 7 µm, focal distance of lens n°1 is 50 mm, focal distance of lens n°2 is 10 mm and the distance between the 2 lenses is 35,7 mm.

Said two scanning mirrors are used to scan the illuminating laser spot across the solid support 11 on which is deposited the specimen containing the microorganisms to be detected. The laser spot moves in the x direction at a speed for example of 1 meter per second.

Said scanning mirrors 16 (=scanner 16) allow, for instance, a line-to-line (y) spacing of 3 µm (distance between two scan lines).

High optical accuracy is required from said scanning means to ensure accurate positioning of the laser spot (scanning lens 17).

Using a laser spot size of 7 µm at a speed of 1 m/s, a 25 mm filter can be scanned in under 3 minutes.

The solid support 11 (such as a filter membrane) on which is deposited the sample to be analyzed is placed on a removable specimen holder, which is used to carry the specimen support from the laboratory, or from where ever the specimen is collected, and to introduce it into the instant apparatus.

The load drawer (not represented) is easily accessible to the user. The removable specimen holder is designed to handle, for instance, a circular solid support and is deposited on the load drawer. The drawer is then pushed into the apparatus and the sample membrane carrying the microorganisms comes directly under the scanner 16. The sample membrane holder is cooled to protect the stability of the labelled microorganism (for instance by Peltier effect).

Said specimen loader cooperates with a mechanism to introduce the sample holder in the apparatus and to automatically bring it with precision at the right distance from the scanning lenses.

The scanner 16 passes the focused laser beam to the target 11, thereby inducing fluorescence from the microorganisms or any fluorescent material.

The thus fluorescent light emitted from the specimen membrane passes through dichroic filters 20 and optical filters 21 to two photomultipliers (PMTs) 30.

Said PMTs 30 detect fluorescence at two wavelengths referred to as the green and the red channels) (centred on 530 nm and 615 nm).

The PMT signals, together with time synchrony information from the scanner 16, are passed to the signal processing system 40.

This system 40 comprises pre-amplifiers 41, signal sampling devices 42 and digital signal processing unit 43.

More precisely, each of said PMT signals is amplified by a dedicated preamplifier 41. The amplified analogue signals are digitized at 2 MHz, using 8-bit resolution (256 signal levels). Each PMT channel has a dedicated digitizer.

The digitized PMT signals are passed to a Digital Signal Processor (DSP) 43.

The signals are then analyzed and the resulting output information is passed through an instrument PC 50, which controls the scanning device, acts as a host for the DSP system 43, stores data during solid support scanning and passes scan results to the user PC 60.

Said user PC system 60 is used to process and display the results of a scan, currently using Matlab® software, as the principal analytical tool.

The instant apparatus has the facility to allow, if necessary, direct observation of any object on the solid support, by driving an automated microscope from the user PC 60.

Figure 8:
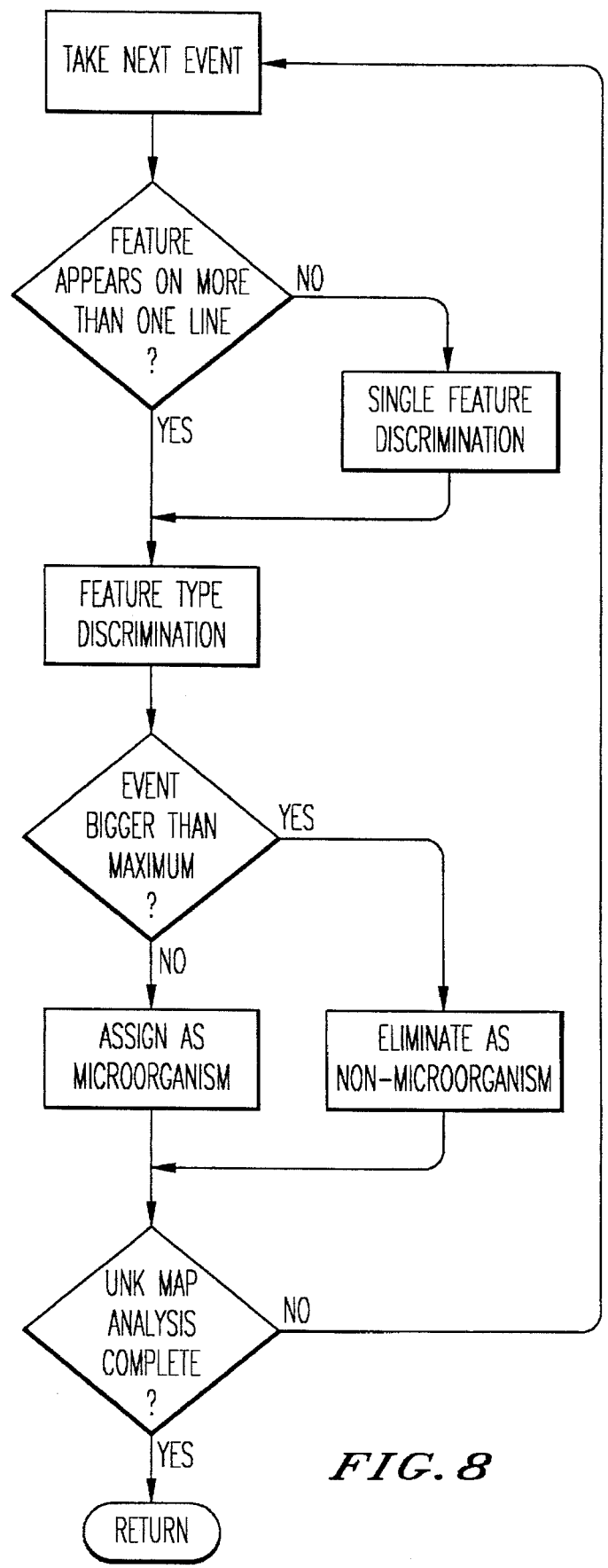
FIG. 8: flow chart showing event size discrimination.

FIGS. 4–8 sum up the different steps of the instant process in view to reject:

background noise (dynamic threshold, FIG. 5),
colour discrimination (FIG. 7),
uncorrelated features (FIG. 6),
size discrimination (FIG. 8).

Effect of Variation on Design Parameters

Figures 9A, 9B:
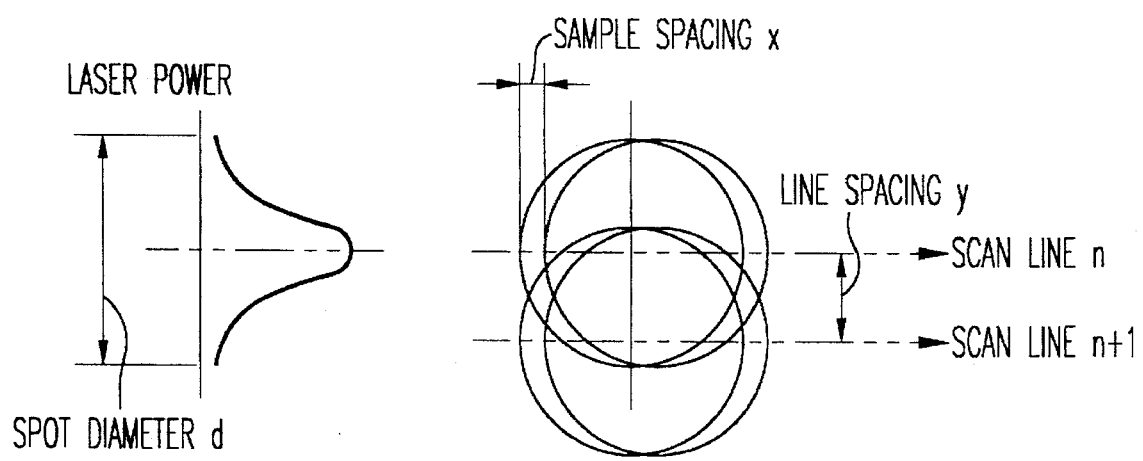
FIG. 9: illustrates the principal scanning paramaters d, x, y.

The following scanning physical parameters: laser spot size (d), scan line sampling (x) and line spacing (y) influence the detection performance of the instant process, as illustrated in FIG. 9. They are:

- d: the scan laser spot dimension. The spot power distribution is Gaussian, and the spot dimension is usually defined as the dimension at which the laser intensity has fallen to ($1/e^2$) of the peak value (approximately 13%).
- x: the distance between successive data samples on one scan line. This is controlled by the sampling rate, and the speed of the scanning mirrors.
- y: the distance between successive scan lines. This is controlled by the step size used to move the scanning mirror.

The effect of varying these parameters is summarised in Table II. It is clear that there is an optimum operating region for each parameter. The size of this region is determined by three principal constraining factors:

- minimising the probability of obtaining false positive or false negative result;
- practical engineering constraints (component tolerances, scanning mirror positional accuracy, etc);
- processing and data analysis system costs (process speed, data storage memory).

TABLE II

| Parameter | Current value | Requirement | Change | Issues and effect of change |
|---|---|---|---|---|
| Spot diameter | 7 μm | Small enough to discriminate two close events | Bigger spot | False-negative due to lower signal level |
| | | | smaller spot | Increased scan time |
| Line spacing y | 3 μm | small enough to see bacteria on 2 consecutive lines | Larger spacing | False-negative if bacteria not seen on 2 lines |
| | | | smaller spacing | mechanical tolerances; data storage; scan time |
| scan line sampling x | 0.5 μm (2 mHz) | Small enough to distinguish noise from real event | Higher spacing (lower sample rate) | Insufficient discrimination |
| | | | Lower spacing (high sample rate) | Mechanical tolerances; data storage; scan time |

Figure 1:
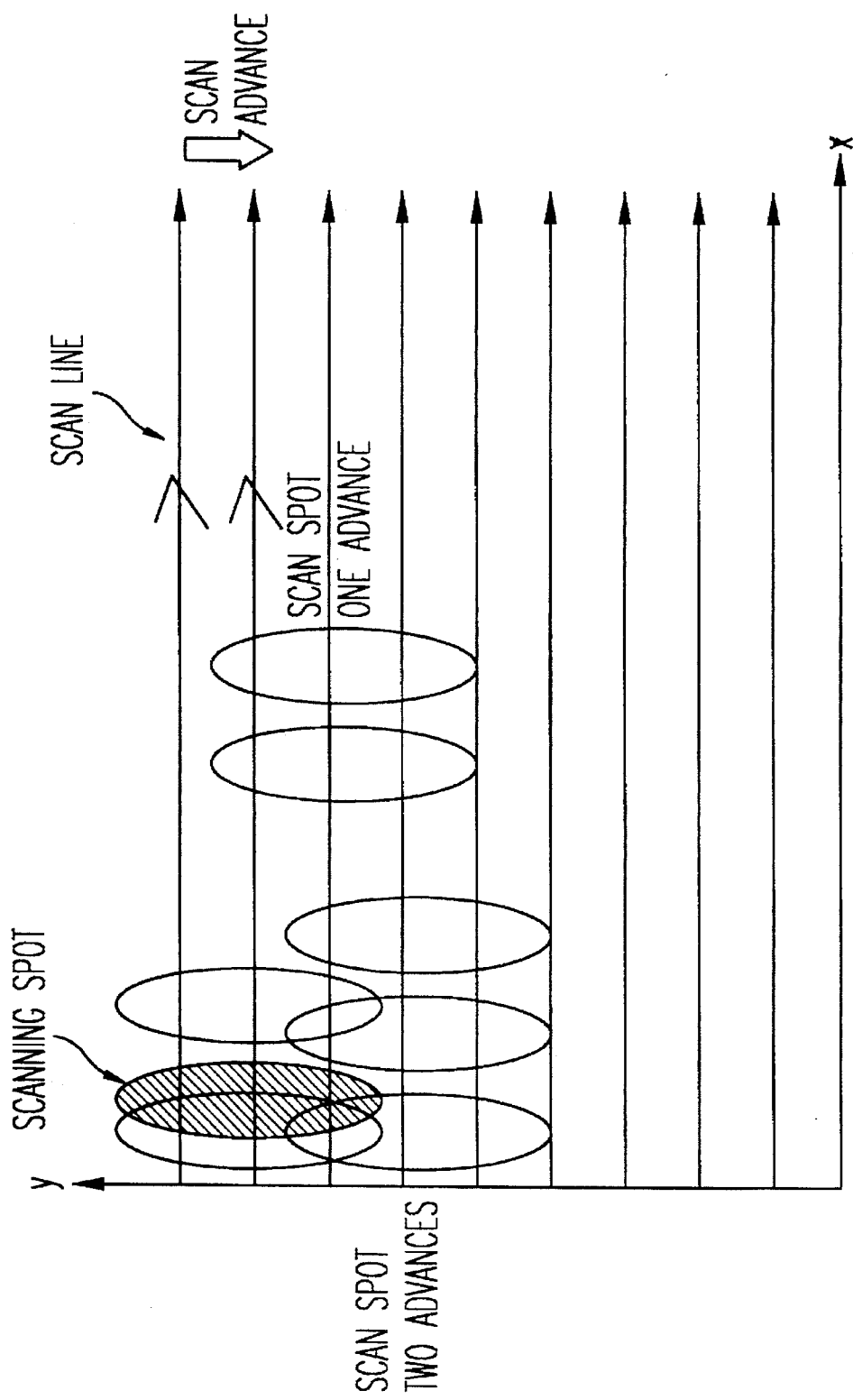
FIG. 1: drawing of overlapping scan pattern showing beam shape, scan pattern, direction and relative dimensions.
Figure 2:
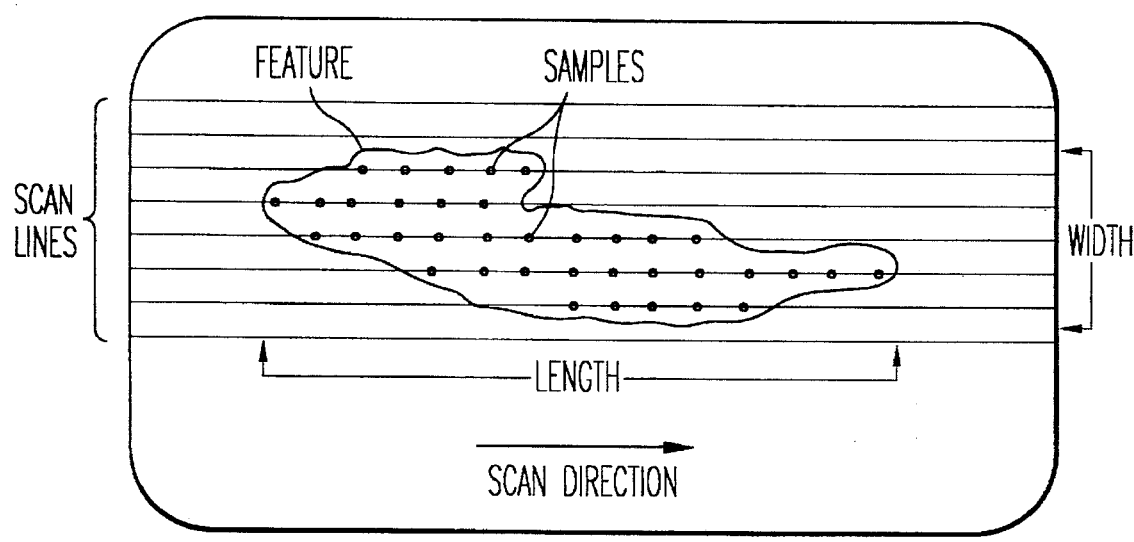
FIG. 2: definition and dimension of an event.
Figure 10:
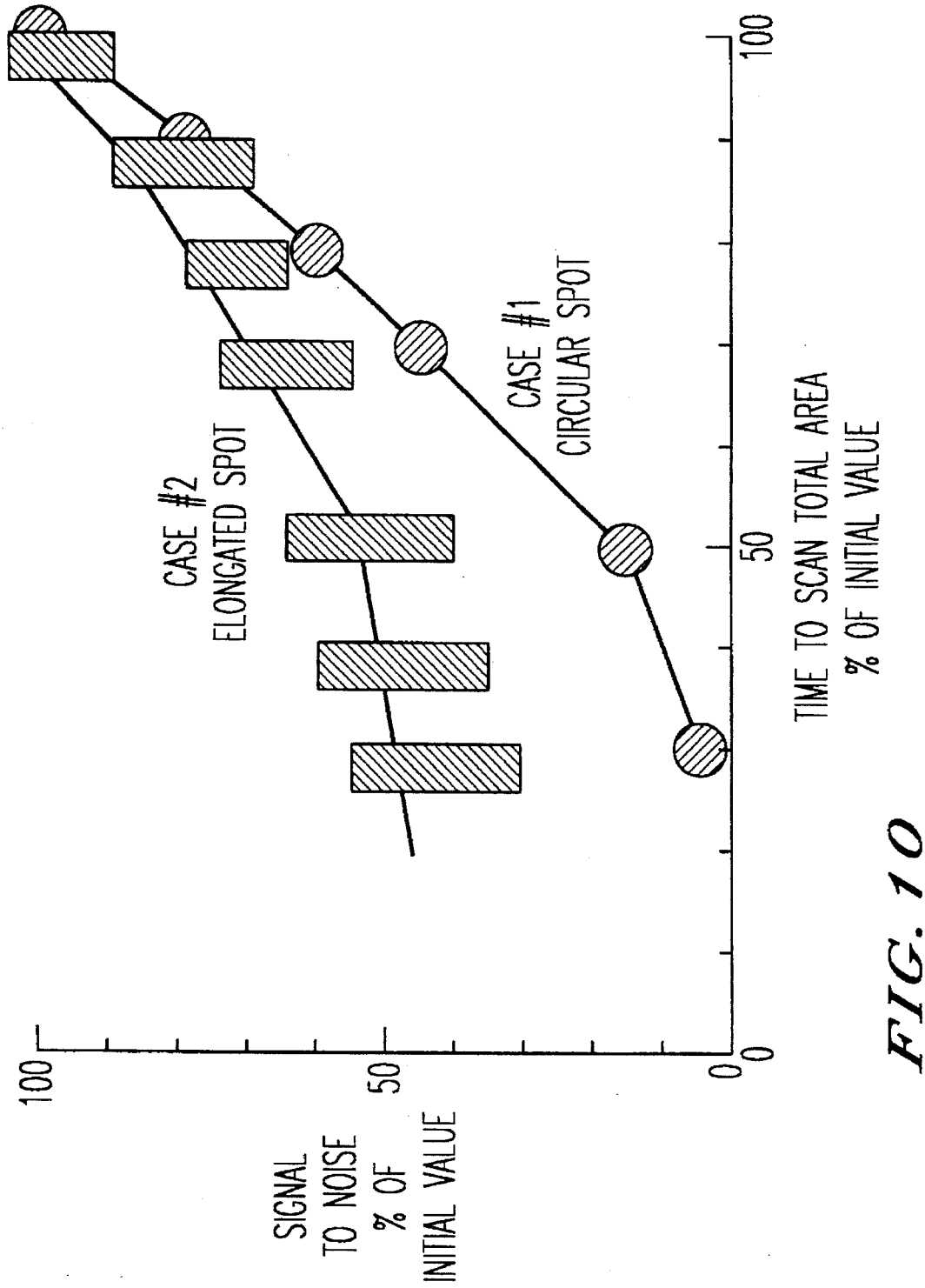
FIG. 10: illustrates a comparison of reduction in signal to noise when the laser spot is circular (Case 1) or elongated (Case 2).

The role of these parameters is also shown in FIGS. 1 and 10.

The target 11 is scanned as shown in FIG. 1. With reference to said FIG. 1, the scan time in terms of laser spot dimension and the SNR may be evaluated as follows:

total area scanned is X.Y
scan velocity is v
retrace time is negligible
spot dimensions are $a_x$ and $a_y$
scan advance is $\Delta y$ Then the time to scan the total area is equal to the time to scan one line times the number of scan lines.

Time per line=X/v
Number of lines=Y/$\Delta y$
Y=$a_y$/n where n is the number times each spot is scanned.
Thus, the time to scan is given by:

$$\text{Scan time} = \frac{X \cdot Yn}{v \cdot a_y}$$

If all things are equal the time to complete a scan is proportional to the area scanned and the number of times each element is scanned. It is inversely proportional to the velocity of scan and the dimension of the spot in the Y direction.

However, all things are not equal and if the scan time is reduced by either the simple expedient of increasing the spot size or the velocity the signal to noise will be compromised.

The signal is proportional to the intensity of illumination (watts/sq.cm.) and the time that each spot is illuminated. The noise is proportional to the square root of the illuminated area and inversely proportional to the scan velocity. Thus, considering that:

- the target microorganism is smaller than the illuminating spot;
- the total laser power is a constant (Io) and is spread over the illuminating spot;
- the scan may be overlapped as described above where n is the number of times each spot is scanned.

The signal to noise can be expressed in terms of familiar quantities:

$$S/N = \frac{Io}{a_x \cdot a_y} \sqrt{\frac{n}{a_y \cdot v}}$$

This demonstrates explicitly how the detection signal to noise is reduced as either the scan speed or laser spot dimension is increased. Even though this equation does not consider the recovery of signal to noise which will be gained by correlation of adjacent scan lines (see FIG. 1).

FIG. 10 shows a comparison of the results of the two equations developed above, under two sets of conditions. In each case, it was assumed that an initial condition existed with a circular laser spot of dimension a. Under this condition, the SNR was 100% and the scan time was 100%.

Condition 1: increase the laser spot dimension at constant velocity maintaining a circular spot and with no overlapping scan.

$n=1$ and $a_x=a_y$

Condition 2: elongate the spot by increasing the y dimension while decreasing the x dimension such that the spot area is constant and overlap so that each spot is scanned twice:

$n=2$ and $a_x=1/a_y$

EXAMPLE 1

Detection of Total Viable Bacteria in Water

An aliquot of water is diluted in a labelling buffer containing a fluorescent marker (fluorescein succimidyl ester). After 5 min at room temperature, the specimen is filtered on a 0.22 µm pore size membrane and analysed using the present invention, with:

d=14 µm (laser diameter spot)

x=2 µm (scan sample spacing)

y=5 µm (scan line spacing).

The basis of the instant process is that the energy falling on a particle can be calculated at any point in the Gaussian beam profile; and all the following parameters can therefore be specified:

scan speed: v=1 m/s laser power (at the laser): L=60 mwatts optical efficiency: $\zeta_o=0.66$ collection efficiency $\zeta=0.01$ power on solid support: $P=\zeta_o.L$ sample time t=2 µs fluorescent conversion: $\eta=2.10^{-3}$ background fluorescence conversion: $\eta_b=10^{-6}$ wavelength of light: $\lambda=0.53$ quantum efficiency: q=0.15 percentage in band: B=0.89

PMT voltage: Z=600 dynode constant $\kappa=0.75$

Figure 12:
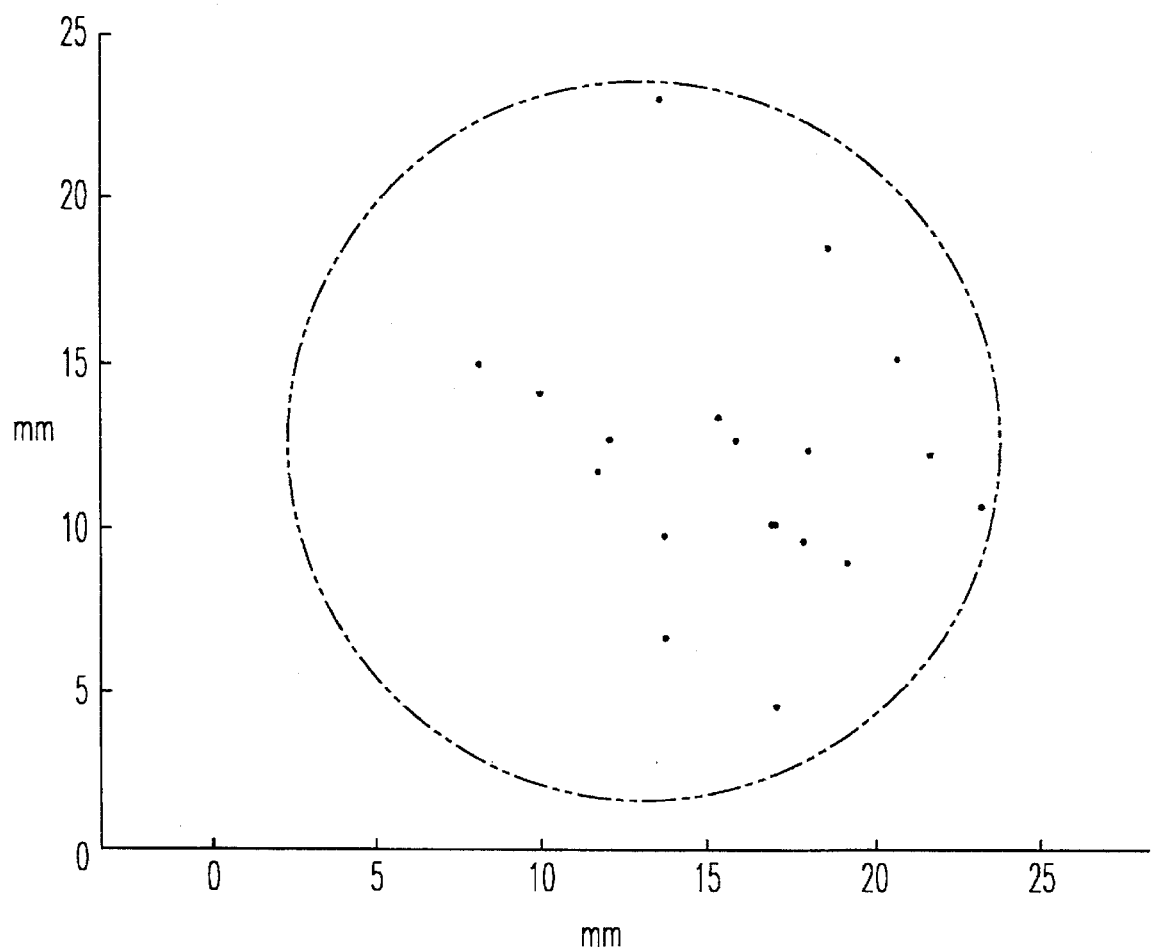

In said conditions the following results may be obtained and are illustrated in Table III and FIGS. 11 and 12, where 19 fluorescent spots (i.e. 19 microorganisms) may be detected.

TABLE III

Reading bnhs 11.002 . . .
Data recorded on: Wed Jul 13 16:36:52 1994
filename = bnhs__11.002
Bursts = 312 Bytes = 7924 Samples = 5044 Features = 310
PMT 1: Samples = 4028 Features = 234
PMT 2: Samples = 1016 Features = 76
bnhs__11.002
Green filter: spots = 55.
Red filter: spots = 30.
   Rejected 17 spots with ratio greater than 0
   Rejected 18 green uncorrelated spots with single features less than 13 samples long
   Rejected 0 green spots greater than 25 samples long
   Rejected 1 green spots greater than 5 lines wide
Overlay: samples = 890, features = 66, spots = 19
End of Data Handler.

EXAMPLE 2

Detection and Counting of Fluorescent Viable Bacteria

Aliquots of culture of different microorganisms are diluted in a saline buffered solution and filtered through an 0,2 µm pore size membrane; retained microorganisms are labelled by addition of 1 ml of labelling solution (viability marker)) followed by a 15 minutes incubation at room temperature.

The resulting fluorescent labelled microorganisms are detected and counted by carrying out the instant process with the parameters illustrated in the following table IV and which can vary according to the type of microorganisms tested.

TABLE IV

DETECTION AND COUNTING OF VARIOUS TYPES OF VIABLE MICROORGANISMS WITH FLUORESCENT VIABILITY MARKERS

| | PARAMETERS SETTING | | | | | BASIC DETECTION RESULTS | | | | | |
| --- | --- | --- | --- | --- | --- | --- | --- | --- | --- | --- | --- |
| | | | Green | Red | Ratio* | | | | | | |
| Micro- | Laser | Spot | PMT | PMT | greater | Green Channel | | | Red Channel | | |
| organisms | power | size | (Volt) | (Volt) | than | Samples | Features | Events** | Samples | Features | Events** |
| Mould spores (penicilium) | 30 mw | 14 µm | 450 | 500 | 1 | 18708 | 1052 | 260 | 5538 | 383 | 178 |
| Yeast | 60 mw | 14 µm | 680 | 850 | 0 | 28284 | 1487 | 348 | 28278 | 1530 | 364 |

TABLE IV-continued

DETECTION AND COUNTING OF VARIOUS TYPES OF VIABLE MICROORGANISMS
WITH FLUORESCENT VIABILITY MARKERS

| (Sacchar. C) | | | | | | | | | | | |
|---|---|---|---|---|---|---|---|---|---|---|---|
| Lactic starter | 60 mw | 14 μm | 680 | 850 | 0 | 5859 | 348 | 112 | 3512 | 192 | 68 |
| E. Coli | 50 mw | 14 μm | 700 | 930 | 0 | 9582 | 543 | 143 | 7662 | 513 | 102 |
| Lacto. sake | 50 mw | 7 μm | 700 | 900 | 0 | 3214 | 208 | 91 | 2849 | 203 | 114 |
| "Stressed" lact Saké | 50 mw | 7 μm | 750 | 900 | 0 | 5706 | 397 | 202 | 2196 | 164 | 104 |

| Micro-organisms | NUMBER OF GREEN EVENTS ELIMINATED BY DISCRIMINATION PROCESS | | | FINAL RESULTS |
|---|---|---|---|---|
| | Ratio | Single Feature | "size" | |
| Mould spores (penicilium) | 0 | 0 | 5 | 255 |
| Yeast (Sacchar. C) | 252 | 14 | 0 | 82 |
| Lactic starter | 63 | 4 | 0 | 45 |
| E. Coli | 41 | 7 | 0 | 95 |
| Lacto. sake | 30 | 2 | 1 | 58 |
| "Stressed" lact Saké | 38 | 119 | 3 | 42 |

It must be pointed out that in said Table IV, "*Ratio" means fluorescent intensity in the red channel divided by fluorescent intensity in the green channel and the columns marked "••" actually include the total of events as defined in the text and the number of uncorrelated features (also called single features).

It is also to be noted that features and events may be found in the red channel only and vice versa and impact of discrimination by Gaussian after other criteria not shown on this Table.

This Table IV shows that fluorescent particles other than relevant microorganisms are eliminated.

We claim:

1. Method for detecting and counting separated fluorescent microorganisms arrayed in two dimensions on a solid support and spaced apart by a distance greater than a diameter of an incident laser beam, comprising the steps of:

scanning said solid support on which a specimen potentially containing microorganisms has been deposited, said specimen having been subjected to fluorescent staining, with the incident laser beam, forming a laser spot having said diameter on the solid support, said laser spot diameter being greater than the microorganism to be detected wherein said laser spot diameter is between 4 and 14 μm, and wherein a distance between two adjacent scanning lines is such that the entirety of the support is scanned at least twice, by partial overlapping of adjacent scanning paths; and simultaneously:

detecting the resultant fluorescent light at least at one wavelength, by selecting as samples only detected signals exceeding a given threshold, wherein a set of adjacent samples on a scan-line represents a feature;

establishing a set of correlated-features by line-to-line correlation of individual features, by comparing features on each pair of adjacent lines in time-synchrony, counting the number of lines over which said set of correlated-features occur, each set of correlated-features forming an event, and eliminating any single uncorrelated-feature;

comparing said correlated-features on each pair of adjacent lines in time synchrony, at least at two different wavelengths $\lambda_1$ and $\lambda_2$ for selecting the correlated-features having an emission intensity ratio at said two wavelengths lower than a predetermined number, said predetermined number being determined by a spectral nature of the fluorescent staining and said predetermined number being specified that if the emission ratio at said wavelength generated by any correlated samples is greater than a predefined value, the complete event is eliminated;

determining if, for retained events, the events energy profile in three dimensions is within predetermined Gaussian shape criteria predetermined by the Gaussian energy profile of the laser beam and rejecting events not within said predetermined Gaussian shape criteria.

2. The method as in claim 1, further comprising a step of size discrimination by:

determining the length of each event by counting the number of selected signals, by starting with the selected signal appearing first on a scanning direction on a feature of said event which occurs the earliest, then continuing to include the selected signal appearing last in the scan direction on a feature that ends last, said counting taking as one selected signal all the correlated selected signals on different scan lines, determining the width of said event by counting the number of adjacent lines covered by the same event and eliminating events for which the number of said counted selected signals is greater than a predetermined number A, and/or the number of said adjacent scan-lines is greater than a predetermined number B wherein said predetermined number A is derived from the Gaussian intensity distribution of the spot as related to a scan line sampling distance and wherein the predetermined number B is derived from the Gaussian intensity distribution of the spot as related to a distance between adjacent scanning lines.

3. A method for detecting and counting separated fluorescent microorganisms arrayed in two dimensions on a solid support and separated by a distance greater than the diameter of an incident laser beam, comprising the steps of:

collecting microorganisms from a specimen on said solid support, such as a filter membrane;

labelling said microorganisms with a dye selected from the group consisting of vital dyes, viability markers, fluorescent substances carried by antibodies or nucleic probes, or generated by an enzyme linked probe system, which, when excited, produce an emission fluorescent at a wavelength $\lambda_1$;

scanning said solid support with said incident laser beam, forming a laser spot having said diameter on said solid support, said laser spot diameter being greater than the microorganism to be detected and wherein said laser spot diameter is between 4 and 14 µm, and wherein a distance between two adjacent scanning lines is such that the entirety of the support is scanned at least twice, by partial overlapping of adjacent scanning paths; and simultaneously:

detecting the resultant fluorescent light at least at one wavelength, by selecting as samples only detected signals exceeding a given threshold, wherein a set of adjacent samples on a scan-line represents a feature;

establishing a set of correlated-features by line-to-line correlation of individual features, by comparing features on each pair of adjacent lines in time-synchrony, counting the number of lines over which said set of correlated-features occur, each of set of correlated-features forming an event, and eliminating any single uncorrelated-feature;

comparing said correlated-features on each pair of adjacent lines in time synchrony, at least at two different wavelengths $\lambda_1$ and $\lambda_2$ for selecting the correlated-features having an emission intensity ratio at said two wavelengths lower than a predetermined number, said predetermined number being determined by a spectral nature of the dye labelling and said predetermined number being specified that if the emission ratio at said wavelength generated by any correlated samples is greater than a predefined value, the complete event is eliminated;

determining if, for retained events, the events energy profile in three dimensions is within predetermined Gaussian shape criteria predetermined by the Gaussian energy profile of the laser beam and rejecting events not within said predetermined Gaussian shape criteria.

4. The method as in claim 3, further comprising a step of size discrimination by:

determining the length of each event by counting the number of selected signals, by starting with the selected signal appearing first on a scanning direction on a feature of said event which occurs the earliest, then continuing to include the selected signal appearing last in the scan direction on a feature that ends last, said counting taking as one selected signal all the correlated selected signals on different scan lines, determining the width of said event by counting the number of adjacent lines covered by the same event and eliminating events for which the number of said counted selected signals is greater than a predetermined number A, and/or the number of said adjacent scan-lines is greater than a predetermined number B wherein said predetermined number A is derived from the Gaussian intensity distribution of the spot as related to a scan line sampling distance and wherein the predetermined number B is derived from the Gaussian intensity distribution of the spot as related to a distance between adjacent scanning lines.

* * * * *